US011471840B2

(12) United States Patent
Le et al.

(10) Patent No.: US 11,471,840 B2
(45) Date of Patent: Oct. 18, 2022

(54) GAS MIXING SYSTEM

(71) Applicant: Billups-Rothenberg, Inc., San Diego, CA (US)

(72) Inventors: Royal Q. Le, San Diego, CA (US); Kyong Son, San Diego, CA (US); Barry E. Rothenberg, San Diego, CA (US)

(73) Assignee: BILLUPS-ROTHENBERG, INC., San Diego, CA (US)

( * ) Notice: Subject to any disclaimer, the term of this patent is extended or adjusted under 35 U.S.C. 154(b) by 232 days.

(21) Appl. No.: 16/718,822

(22) Filed: Dec. 18, 2019

(65) Prior Publication Data

US 2020/0188865 A1 Jun. 18, 2020

Related U.S. Application Data

(60) Provisional application No. 62/781,183, filed on Dec. 18, 2018.

(51) Int. Cl.
*B01F 23/00* (2022.01)
*B01F 23/10* (2022.01)
(Continued)

(52) U.S. Cl.
CPC ........ *B01F 23/19* (2022.01); *B01F 25/43141* (2022.01); *B01F 35/2111* (2022.01);
(Continued)

(58) Field of Classification Search
CPC ... B01F 23/19; B01F 35/2111; B01F 35/2211; B01F 35/2132; B01F 25/43141; B01F 2101/44; C12M 41/34
See application file for complete search history.

(56) References Cited

U.S. PATENT DOCUMENTS 3,762,428 A * 10/1973 Beck ........................ B01F 23/19 137/88
4,257,439 A * 3/1981 Mayeaux ................ B01F 23/19 422/111
(Continued)

OTHER PUBLICATIONS

Bakmiwewa, et al., "An effective, low-cost method for achieving and maintaining hypoxia during cell culture studies," Bio Techniques, Oct. 2015; 59:223-229.
(Continued)

*Primary Examiner* — Anshu Bhatia
(74) *Attorney, Agent, or Firm* — Umberg Zipser LLP

(57) ABSTRACT

Provided herein are gas mixing systems, comprising a gas inlet for receiving two or more gases and a mixing chamber with a static mixer for mixing the gases. Preferred mixing chambers further comprise a reduced pressure compartment downstream of the static mixer that is in fluid communication with the gas inlet. A gas outlet is in fluid communication with the mixing chamber, and one or more sensors are coupled to the reduced pressure compartment and are configured to continuously sense various parameters such as barometric pressure and the percentage of oxygen in the gas mixture moving through the mixing device. Most typically, the readings of the sensor are pre-compensated for temperature, pressure, and humidity. Also provided herein are methods for using the same.

20 Claims, 4 Drawing Sheets

(51) Int. Cl.

| | |
|---|---|
| ***C12M 1/34*** | (2006.01) |
| ***B01F 25/4314*** | (2022.01) |
| ***B01F 35/21*** | (2022.01) |
| ***B01F 35/221*** | (2022.01) |
| *B01F 101/44* | (2022.01) |

(52) U.S. Cl.

CPC ...... *B01F 35/2132* (2022.01); *B01F 35/2211* (2022.01); *C12M 41/34* (2013.01); *B01F 2101/44* (2022.01)

(56) References Cited

U.S. PATENT DOCUMENTS

| | | | | |
|---|---|---|---|---|
| 4,989,637 | A | 2/1991 | Dittrich | |
| 8,241,904 | B2 | 8/2012 | Cheng et al. | |
| 8,551,770 | B2 | 10/2013 | Fraker et al. | |
| 9,175,254 | B2 | 11/2015 | Fraker et al. | |
| 2006/0263283 | A1* | 11/2006 | Egan | B01F 23/19 423/210 |
| 2007/0089796 | A1* | 4/2007 | Electra Brown | G05D 11/03 137/896 |
| 2012/0201092 | A1* | 8/2012 | Hatano | B01F 25/3131 366/150.1 |

OTHER PUBLICATIONS

Yazdani, Mazyar, “Technical aspects of oxygen level regulation in primary cell cultures: A review,” Interdiscip Toxicol., 2016; 9(3-4):85-89.

* cited by examiner

GAS MIXING SYSTEM

This application claims priority to our copending US Provisional Patent Application with the Ser. No. 62/781,183, which was filed Dec. 18, 2018, and which is incorporated by reference herein.

FIELD OF THE INVENTION

The field of the invention relates to devices and methods for mixing gases, particularly as it relates to the provision of tightly controlled gas mixtures in the field of in vitro cell and/or tissue culture.

BACKGROUND

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Molecular oxygen (i.e., $O_2$) is essential for aerobic respiration. While the concentration of oxygen in the atmosphere is approximately 21%, cells derived from multicellular eukaryotes, especially animal cells, are generally adapted to lower oxygen levels. Thus, it is generally desirable for in vitro cultures of such mammalian cells to expose the cells to specific amounts of oxygen in the cell culture chamber for optimal growth. In most cases, the amount of oxygen is lower than that of the atmosphere. With increasing interest in the performance of cell culture experiments under various oxygen levels, a range of technologies and instruments have been developed.

For example, U.S. Pat. No. 8,551,770 discloses a cell culture apparatus for culturing cells that provides enhanced oxygen delivery and supply to cells without the need for stirring or sparging. Oxygen diffusion occurs on both sides of the culture vessel, top and bottom. A gas-permeable membrane that includes perfluorocarbons in its composition allows for the rapid, enhanced and uniform transfer of oxygen between the environment of cells or tissues contained in the cell culture container apparatus and the atmosphere of the incubator in which the cell culture apparatus is incubated. However, a method for controlling the specific amounts of oxygen is not disclosed in the patent. Thus the cell culture apparatus does not provide control over the condition under which the cells are grown, particularly as it relates to the amount of oxygen.

U.S. Pat. No. 4,989,637 discloses a gas mixing apparatus for the generation of a continuous gas mixture stream consisting of a main stream of a carrier gas to which one or more gas components are added in measured quantities. However, this apparatus does not allow complete control on the percentage of oxygen in the gas mixture. In still further known devices and methods, $N_2$ and $CO_2$ (see e.g., OKOlab $CO_2$-$O_2$ controller) are mixed and fed into an incubator, and a slipstream of the mixed gas or gas in the incubator can be dried and routed back to a controller. While such and similar devices are at least conceptually effective, various disadvantages nevertheless remain. Among other things, the relatively large dead volume renders fast and accurate adjustments problematic. Alternatively, external gas mixing devices can be used in conjunction with oxygen and $CO_2$ sensors disposed in an incubator. However, and as before, the relatively large dead volume of an incubator makes fast and accurate adjustments very difficult. To overcome such disadvantages, predefined gas mixtures can be supplied from a pressurized gas tank to so ascertain a precise oxygen and/or $CO_2$ level. However, such gas supplies are limited to a single type of gas mixture and as such only suitable for a highly limited number of experiments.

Thus, even though various devices and methods for preparing gas mixtures for cell cultures are known in the art, all or almost all of them suffer from various disadvantages. Consequently, there is a need to provide improved devices and methods that provide gas mixtures in a tightly controlled manner that can be quickly and accurately adjusted.

SUMMARY OF THE INVENTION

The inventive subject matter is directed to devices, systems and methods for mixing gases, comprising a gas inlet for receiving two or more gases, a mixing chamber for mixing the gases, wherein the mixing chamber comprises a static mixer and a reduced pressure compartment, wherein the mixing chamber is in fluid communication with the gas inlet; and a sensor mounted on the reduced pressure compartment, and configured to continuously sense the amount and/or percentage of oxygen in the gas mixture. Preferably, the reduced pressure compartment may have a lollipop shape or otherwise extend from the mixing chamber.

Therefore, in one aspect of the inventive subject matter the inventors contemplate a gas mixing and analytic system that includes a gas inlet that is fluidly coupled to a mixing chamber that comprises a static mixer, wherein the mixing chamber further comprises a reduced pressure compartment that is downstream of the static mixer. Preferably, one or more sensors are fluidly coupled to the reduced pressure compartment, wherein the sensors are electronically coupled to a memory for data storage. A gas outlet is in fluid communication with the mixing chamber. Typically, the mixing chamber has a relatively small volume relative to a gas consuming device downstream of the gas mixing and analytic system (e.g., volume of less than 50 ml, or less than 30 ml, or less than 15 ml).

Most typically, but not necessarily, the static mixer comprises a plurality of baffles (e.g., configured to split incoming gas several times). In further embodiments, the reduced pressure compartment comprises a portion having a lollipop shape and may include internal ridges for further mixing. Where desired, a display screen is coupled to a microprocessor and operable to continuously display information sensed by the one or more sensors.

It is also contemplated that the gas mixing and analytic systems presented herein will include a first and a second gas source that are fluidly coupled to the gas inlet. For example, the first and second gas sources may be coupled to respective flow meters that control flow of the gases from the first and second gas sources, and that the respective flow meters are fluidly coupled to the gas inlet. Thus, the gas inlet may be configured to receive a mixture of gases from the first and second gas sources.

Consequently, the inventors also contemplate a method of mixing two or more gases and determining the percentage of oxygen in the gas mixture. Most typically, such method will include a step of providing from a first and a second gas source respective first and second gases, and feeding the first and second gases into a gas inlet of a mixing and analytic system. Preferably, the mixing and analytic system includes a mixing chamber that is fluidly coupled to the gas inlet and comprises a static mixer that mixes the first and second gases to produce a gas mixture, wherein the mixing chamber further comprises a reduced pressure compartment, and wherein one or more sensors are fluidly coupled to the reduced pressure compartment. In another step, the one or more sensors are used to determine the percentage of oxygen in the gas mixture while the mixed gas flows through the mixing and analytic system. The gas mixture is then delivered though a gas outlet to an incubator, wherein the gas outlet is in fluid communication with the mixing chamber.

In contemplated embodiments, flow of the first and second gases are individually regulated before entering the gas inlet. In addition, it is contemplated that the static mixer comprises a plurality of baffles that mix the first and second gases to form a gas mixture. Typically, the gas mixture is fed past the reduced pressure compartment at a flow rate that generates a reduced pressure in the reduced pressure compartment. Where desired, the gas mixture may be further mixed in the reduced pressure compartment using internal ridges in the reduced pressure compartment. Oxygen (and/or $CO_2$) content in the gas mixture is then measured using the one or more sensors and displaying the oxygen content on a display screen of the mixing and analytic system.

As will be readily appreciated, feeding the first and second gases may also include a step of adjusting flow of at least one of the first and second gases. For example, the first and second gas sources may be coupled to respective flow meters that control flow of the gases from the first and second gas sources wherein the respective flow meters are coupled to the gas inlet. Therefore, the gas inlet may be configured to receive a mixture of the gases from the first and second gas sources. Most typically, contemplated methods will also include a step of collecting and storing sensor data in a memory of the mixing and analytic system.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
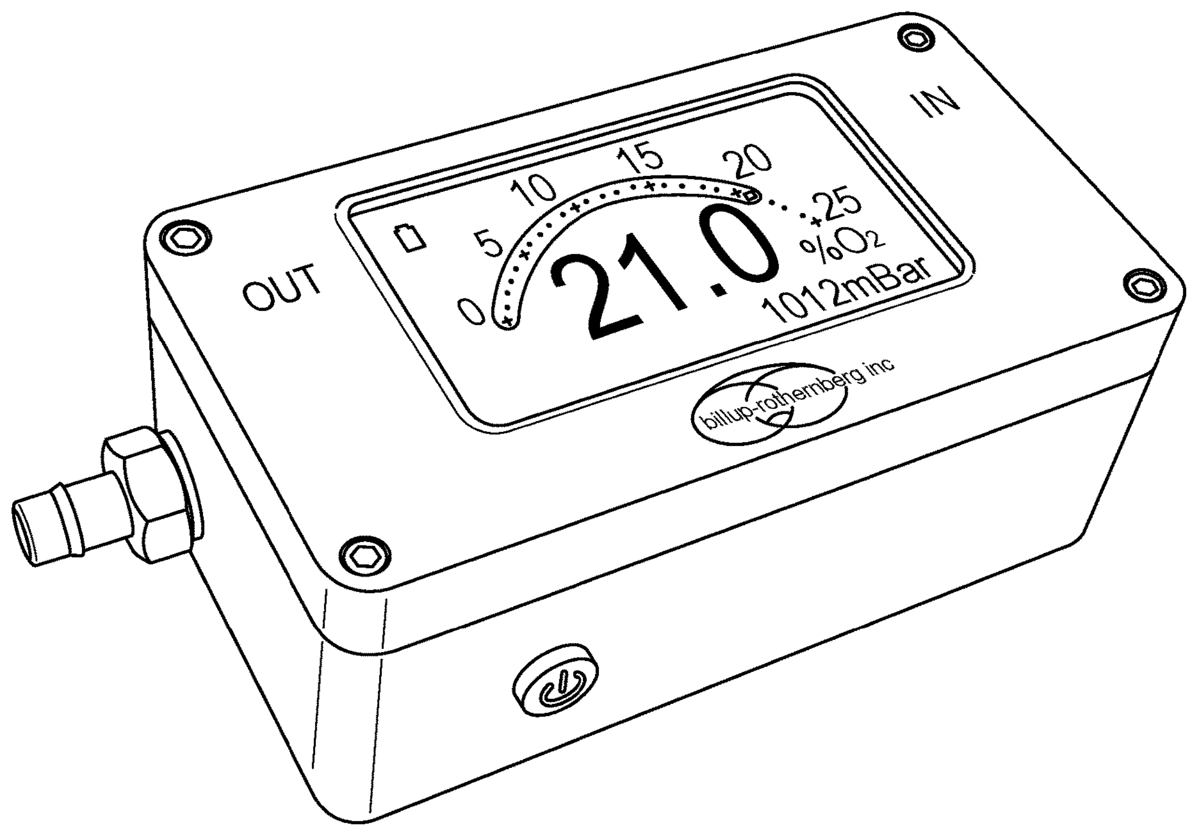
FIG. 1 is one exemplary photograph of one embodiment of the gas mixing and analytic system disclosed herein.

The following discussion provides many example embodiments of the inventive subject matter. Although each embodiment represents a single combination of inventive elements, the inventive subject matter is considered to include all possible combinations of the disclosed elements. Thus, if one embodiment comprises elements air, nitrogen, and oxygen, and a second embodiment comprises elements oxygen and carbon dioxide, then the inventive subject matter is also considered to include other remaining combinations of air, nitrogen, oxygen, or carbon dioxide, even if not explicitly disclosed.

The inventive subject matter as disclosed herein comprises a gas mixing system, comprising an inlet, a mixing chamber, a reduced pressure compartment that is downstream of the static mixer, and one or more sensors coupled to the mixing chamber and/or reduced pressure compartment, and an outlet that delivers a mixed gas stream. The inventors have found that for optimal in vitro tissue culture growth or cell growth, the percentage of oxygen in the system should be less than 21%, and in many cases the specific amount of oxygen is specific to each organ or tissue being cultured. Oftentimes, the oxygen in the cell culture incubator is hard to control due to leaks, human errors, or degraded seal gaskets causing gas leakage. Moreover, the gas introduced in the incubator must be blended well before being introduced to the incubator, to prevent pockets of air having high and/or low amounts of one gas. To overcome these problems faced in the industry, the inventors developed a gas mixing system as disclosed herein. The system provided herein has several advantages over currently known technologies, such as rapid and inexpensive mixing of gases, compact size, measures percentage of oxygen and barometric pressure with high accuracy, factory calibration, and ease of use due to self-calibration.

In one embodiment, the gas inlet of contemplated gas mixing systems receives two or more gases that are to be mixed in the mixing chamber. Most typically, the gases are fed to the inlet as a combined stream of gas that may be at least partially mixed. The gases are usually stored in pressurized gas tanks, and connected to the inlet of the gas mixing system by a tube. A variety of gases may be used, such as, air, oxygen, nitrogen, argon, carbon dioxide, or combinations thereof. To attain the desired cell culture growth conditions air or oxygen must be missed with other gases. Nitrogen and argon are contemplated to be useful in mixing with air because these are inert gases, and does not undergo chemical reactions under experimental conditions. Carbon dioxide may also be used. One advantage of using carbon dioxide is that it interacts with the bicarbonate buffer in the cell culture medium, stabilizing the pH at about the optimum level (~7.4). As will be readily appreciated, the flow of distinct gases may be regulated independently via one or more flow control devices that may feed the distinct gases to a downstream flow valve to control total gas flow rate. Therefore, the gases delivered to the gas inlet of the device are typically partially mixed (i.e., total gas stream has high local variability in gas content of a single component).

The mixing chamber as described herein is a chamber for mixing the gases that are received from the inlet. In preferred embodiments, the mixing chamber comprises a static mixer fluidly coupled and a downstream reduced pressure compartment. The mixing chamber is in fluid communication with the gas inlet and mixes the gases received from the inlet. This avoids non-homogenous gas concentration in the reduced pressure compartment. The reduced pressure compartment preferably comprises internal ridges that induce turbulence to mix the air. A variety of shapes are contemplated for the reduced pressure compartment. In one embodiment, it has a shape that can be likened to a balloon or portion of a balloon. In another embodiment, the reduced pressure chamber has a shape that can be likened to a lollipop. Preferably, the reduced pressure chamber includes one or more sensors that can sense the quantity of one or more distinct gases in the reduced pressure chamber. Additionally, sensors may also be used that measure the temperature, pressure, and humidity of the gases being mixed. Most typically, the reduced pressure chamber is offset from the path of air flowing from the static mixer, typically inducing a venturi effect that reduces pressure of the gas in the reduced pressure chamber, which will further facilitate intimate mixing of the gas components in the gas mixture leaving the static mixer.

Besides having a low-pressure compartment for mixing the air, the mixing chamber may also comprise a static mixer (typically upstream of the reduced pressure chamber). The static mixer is contemplated to comprise one or more baffle sets, for example 1-12 baffle sets, or more preferably 2-11 baffle sets, or more preferably 3-10 baffle sets, or more preferably 4-9 baffle sets, or more preferably 5-8 baffle sets, or more preferably 6-7 baffle sets, or more preferably 6 baffle sets. When the static mixer comprises 6 baffle sets, the incoming air is split 64 times to allow mixing. The static mixer is contemplated to be in fluid communication with the reduced pressure compartment, which in turn is in fluid communication with the gas outlet. It should thus be appreciated that a (premixed) stream of gases entering the gas inlet is thoroughly mixed in the static mixer portion as the stream of gases passes through the device. Upon exit of the intimately mixed gas stream, a portion is drawn via venturi effect into the reduced pressure chamber where further mixing occurs. As such, a real-time measurement of a near perfectly mixed gas stream is enabled as gas streams through the device. The so mixed gas stream then leaves the device through an outlet. Viewed from a different perspective, adjustments to the component ratio of gases made upstream of the device can be accurately and rapidly determined without the need for measuring the components in an incubator using sensors present in an incubator.

Therefore, in preferred embodiments, the gas inlet first comes in contact with the static mixer. At least a portion of the gas mixture from the static mixer then flows into the reduced pressure compartment, and the mixed air then goes through the gas outlet. In other embodiments, the gas inlet may first come into contact with the reduced pressure compartment, and then the static gas mixture, followed by the gas outlet.

The gas mixing system as disclosed herein may comprise more than one mixing chambers. One or more of these mixing chambers is contemplated to mount a sensor. Thus, for example, there may be four mixing chambers in the gas mixing system, and each of those mixing chambers have a sensor mounted to it. In this case, the sensor output reading would be an average of the measurement by each chamber. In another example, there may be four mixing chambers in the gas mixing system but only one of them has a sensor mounted to it. The mixing chamber as disclosed herein provides dynamic gas mixture preparation, and allows for complete control over final gas composition. In one embodiment contemplated herein, medical grade gases are used.

The gas mixing system also comprises an outlet in fluid communication with the mixing chamber. The outlet provides the mixed gases to incubator chambers. For example, the outlet may be connected to a cell culture incubator by a tubing. As mentioned above, seal integrity is vital for this system. Thus, in one embodiment, the cell culture incubator and the tubing connecting the cell culture incubator to the mixing chamber are flushed with the desired gas mixture and then tightly sealed. The sealing may be with an O-ring or a silicone stopper. As is known to a skilled artisan, other sealants commonly known in the art may be used as well.

One or more sensors may be in fluid communication with the mixing chamber and/or the reduced pressure chamber. For example, in one embodiment, a sensor may be coupled to reduced pressure chamber (e.g., having a lollipop shape structure wherein the lollipop shape structure provides a reduced pressure compartment for mixing gases). Several different types of sensors are contemplated to be present in the gas mixing system, such as an oxygen sensor, a barometric pressure sensor, a temperature sensor, and a humidity sensor, and wherein the oxygen sensor senses the quantity of oxygen, the barometric pressure sensor senses the barometric pressure, a temperature sensor senses the temperature, and a humidity sensor senses the humidity of the gas in the gas mixing system. In one embodiment, the sensor measures ambient oxygen partial pressure (pO2).

It should be especially noted that internal pressure, temperature, and humidity sensors enable the gas mixing system to integrate these additional sensor readings and convert the pO2 reading to an oxygen percentage (% $O_2$). The gas mixing system may comprise a display screen that display information determined by the sensor, such as the barometric pressure and the percentage of different gases in the gas mixture. The measurement done by the sensor is in a continuous manner. In one embodiment, the sensor may further sense battery life, and may display a variation in color to indicate battery life. For example, the sensor screen may turn red when the battery is low to indicate to a user that the battery should be changed.

In one embodiment, the sensor may be mounted on the lollipop shape structure of the mixing chamber by using an O-ring. The O-ring is useful for preventing gas leakage. Seal integrity is a vital part of this system because debris blockage, human error, and degraded seal gaskets may cause air leakage.

In one embodiment, the sensor has a rechargeable battery, such as a $LiFePO_4$ battery. When a rechargeable battery is used, a longer operational life and maintenance free use of the battery is contemplated.

In one embodiment, the sensor is an integrated solid-state sensor that does not need replacement or re-calibration like conventional electro-chemical or galvanic sensors. The readings are factory calibrated to compensate for ambient temperature, pressure and humidity, enabling accurate operation over a wide environmental range. The system is easy to operate, very stable and robust, does not contain hazardous materials and has negligible cross sensitivity to other gases (e.g., $CO_2$ and $N_2$).

As described throughout this disclosure, the gas mixing system comprises a flow-through $O_2$ sensor providing fast oxygen readings from 0% to 25%. In one embodiment, it may be used in tandem with a gas flow meter. The gas flow meter may be a single flow meter that controls the gas flow of premixed gases, or it may be is a dual flow meter that mixes gases in addition to controlling the gas flow rate.

The devices and systems disclosed herein are ideal for accurately mixing custom $O_2$ and $CO_2$ concentrations for hypoxic and culture conditions or where special pre-mixed gases are expensive or unavailable. Pure gases allow researchers to tailor gas mixtures to their own requirements, but they require onsite blending before use. The gas mixing system disclosed herein provides such blending. The blending is usually done in a reduced pressure compartment. The reduced pressure gas mixing compartment is contemplated to have a volume sufficient to enable the efficient mixing of the gases, such as a volume of at least 0.01 mL, more preferably at least 0.1 mL, or more preferably at least 1 mL, or more preferably at least 5 mL, or in some cases higher than 5 mL. However, complete mixing of the gases in the mixing compartment is not required because the gases would continue to mix upstream of the mixing chamber.

The flow rates of the gases disclosed herein may be 0-20 SCCM (Standard Cubic Centimeter per Minute), 20-40 SCCM, 40-100 SCCM, and up to 1000 SCCM. The flow rate may depends on the volume of the gas mixing compartment, for example, a smaller gas mixing compartment is likely to have a lower gas flow rate. The flow rate of the gas may also depend on the conduit volume in the inside of the device relative to the low pressure structure, for example, is at least 2:1, or 3:1, or 4:1.

The mixing of the gases disclosed herein is contemplated to be both passive and/or active mixing. Active mechanical mixers, such as those utilizing impellers of various configurations are known in the art and may be used in the mixing chamber. Passive, non-mechanical mixers are contemplated in the conduits upstream of the mixing chamber to continue mixing the gas.

Also disclosed herein is a method of mixing two or more gases and determining the percentage of oxygen in the gas mixture. The method comprises providing two or more gas tanks, wherein the gas tanks comprise pressurized gases; providing a gas mixing system comprising a gas inlet for receiving gas from two or more gas tanks, a mixing chamber for mixing the gases, wherein the mixing chamber comprises a lollipop shape structure and is in fluid communication with the gas inlet; a mixture outlet in fluid communication with the mixing chamber; and a sensor mounted on the lollipop shape structure; wherein the sensor is configured to sense barometric pressure and percentage of oxygen in the gas mixture, wherein the sensor readings are compensated for temperature, pressure, and humidity. The one or more gas sensors are contemplated to be pressure and temperature compensated, enabling accurate operation over a wide environmental range without the need for additional calibration.

As is known to a skilled artisan in the art, the amount of a gas is related to the pressure and temperature by the ideal gas law, which is often written as PV=nRT, where P, V and T are pressure, volume, and temperature, n is the number of moles of gas, and R is the ideal gas constant. Thus change in temperature, pressure, and/or volume inside the gas mixing chamber may lead to a change in amount of a gas, such as oxygen. The instant system disclosed herein compensates for such changes in pressure and temperature to accurately read the amount of oxygen and carbon dioxide present in the gas mixing system. Furthermore, unlike other oxygen sensor technologies available in the market, the instant system of sensors for oxygen sensing devices are stable and do not contain lead or any other hazardous materials. The one or more sensors The system is further contemplated to comprise a display screen configured to continuously display information determined by the one or more sensors. Thus, the display screen may display the amount of oxygen, the amount of carbon dioxide, the temperature, the pressure, humidity, and/or battery life in a continuous manner.

In one embodiment, the system may also comprise a real time clock to record and store accurate date and time of measurement of the sample. The system further comprises a data storage device that logs and stores the information gathered by the one or more sensors, such as the oxygen sensor and/or the carbon dioxide sensor. The system is adapted to log and store such data for multiple measurements over time. In some embodiments, the system can log data from the one or more sensors every 60 minutes, or more preferably every 45 minutes, or more preferably every 30 minutes, or more preferably every 15 minutes, or more preferably every 1 minute, or more preferably every 30 seconds, or more preferably every 15 seconds, or most preferably every 5 seconds. The data may be stored for a large number of data points, for example between 10-10,000 data points. The data logging and storage unit can log and store data over a long time, for example up to 6 hours, or more preferably up to 12 hours, or more preferably up to 24 hours or more preferably up to 36 hours or more preferably up to 48 hours, or most preferably up to a week.

Figure 2:
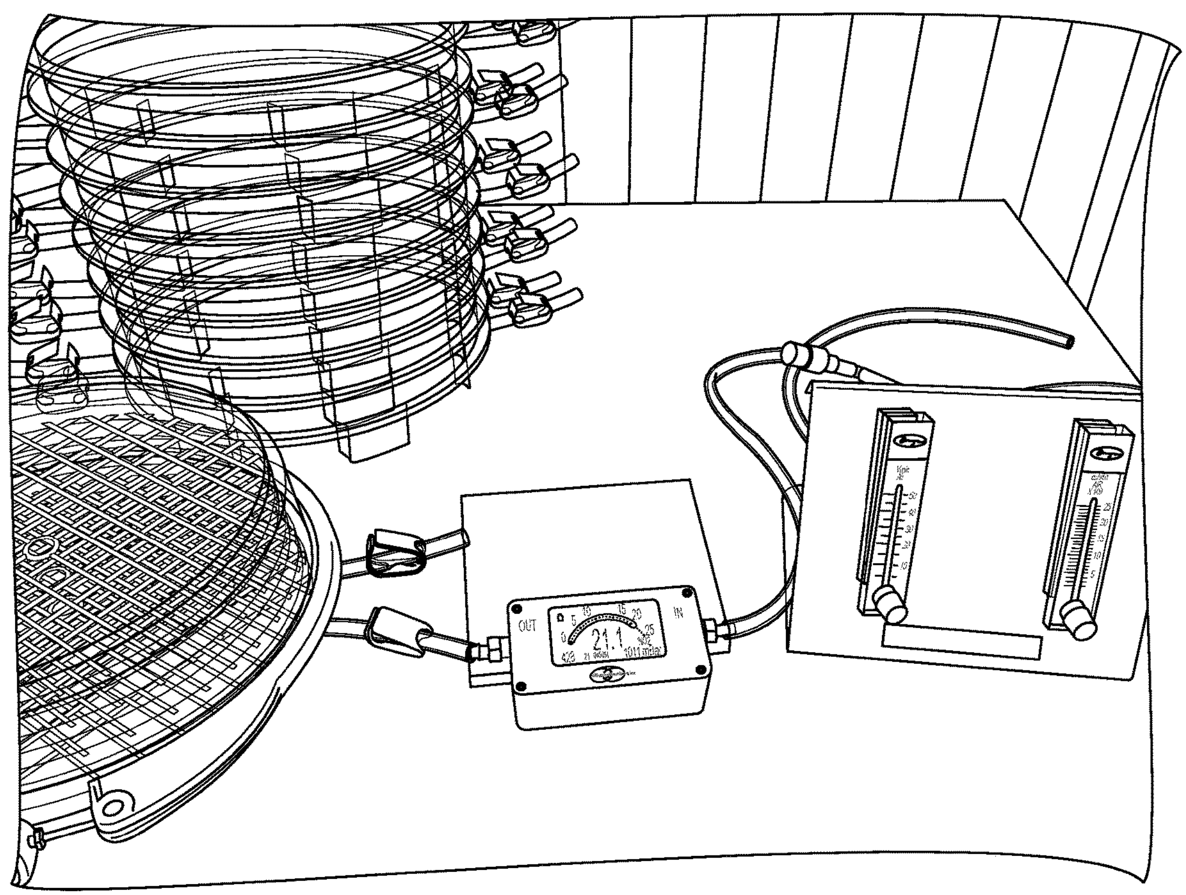
FIG. 2 is another exemplary photograph of the gas mixing and analytic system of FIG. 1 coupled to a dual flow meter for two distinct gases and coupled to a modular incubator chamber.

FIG. 1 illustrates one exemplary photograph of the gas mixing and analytic system 100 disclosed herein, showing the inlet, the outlet, and the sensor display, displaying the oxygen level and the barometric pressure. FIG. 2 demonstrates the use of the gas mixing device with a dual flow meter and a modular incubator chamber. The two bottom tubes are attached to the gas tanks, while the upper tubing with pressure release valve is attached to the connector marked "in." The connector on the left side of the enclosure is attached to the modular incubator chamber. The gas mixing device is further contemplated to comprise a compartment for a battery, such as a 9V battery. FIG. 1 shows the red on/off switch black power button on the side of the gas mixing device. After turning on the gas mixing device, it will typically warm up and stabilize for 15-30 seconds. The number at the bottom life of the display screen reads the amount of power remaining in the battery. The gas mixing system measures percentage of oxygen and barometric pressure which can be seen on the middle of the display screen and right hand corner of screen, respectively.

Figure 3:
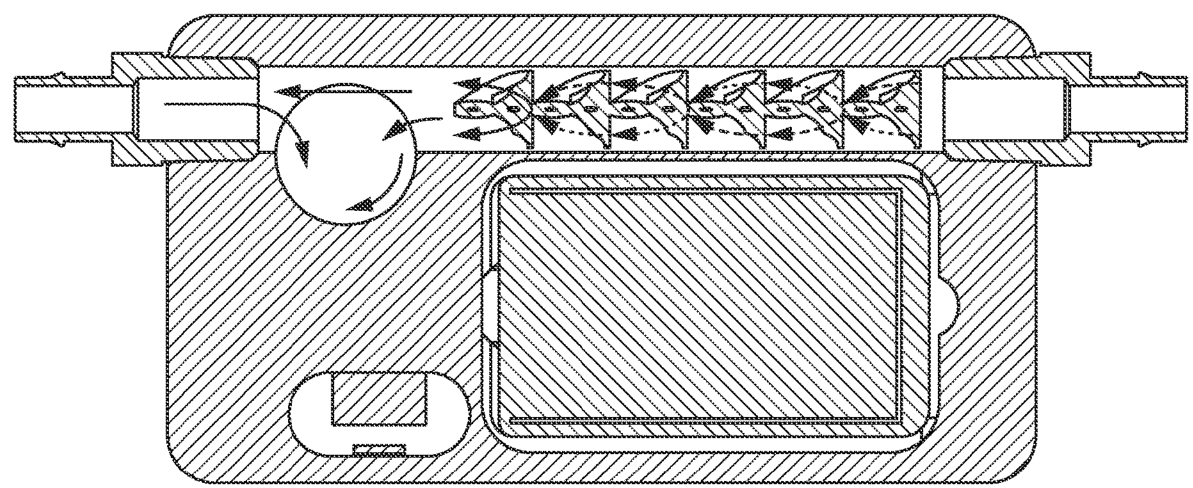
FIG. 3 is an exemplary schematic illustration of a gas mixing and analytic system in operation illustrating the flow of gas in the gas mixing compartment.
Figure 4:
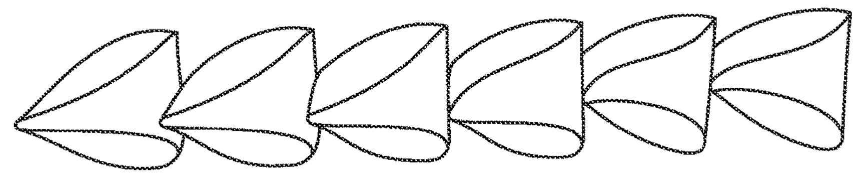
FIG. 4 discloses one exemplary embodiment of a six-baffle set.

FIGS. 3-6 further illustrate embodiments of the gas mixing device disclosed herein. The mixing chamber comprises two important components: a static mixer and a reduced pressure compartment. The static mixer disclosed herein is shown in clear green color. The static mixer as illustrated in FIGS. 3-4 comprises 6 baffle sets which will split the incoming air 64 times. Other embodiments of the static mixer comprising, for example 1-12 baffle sets, are also contemplated herein. The reduced pressure compartment is preferably comprised of internal ridges which induce turbulence to mix the air while maintaining flow and minimizing back pressure.

Figure 5:
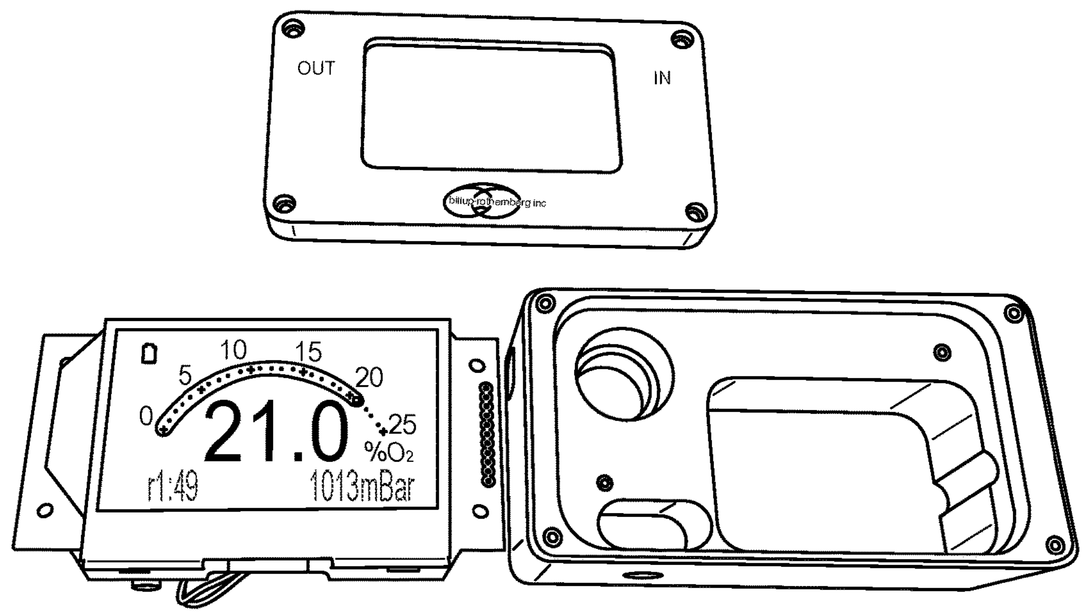
FIG. 5 discloses one exemplary embodiment of the casing of the gas mixing system and the oxygen display.
Figure 6:
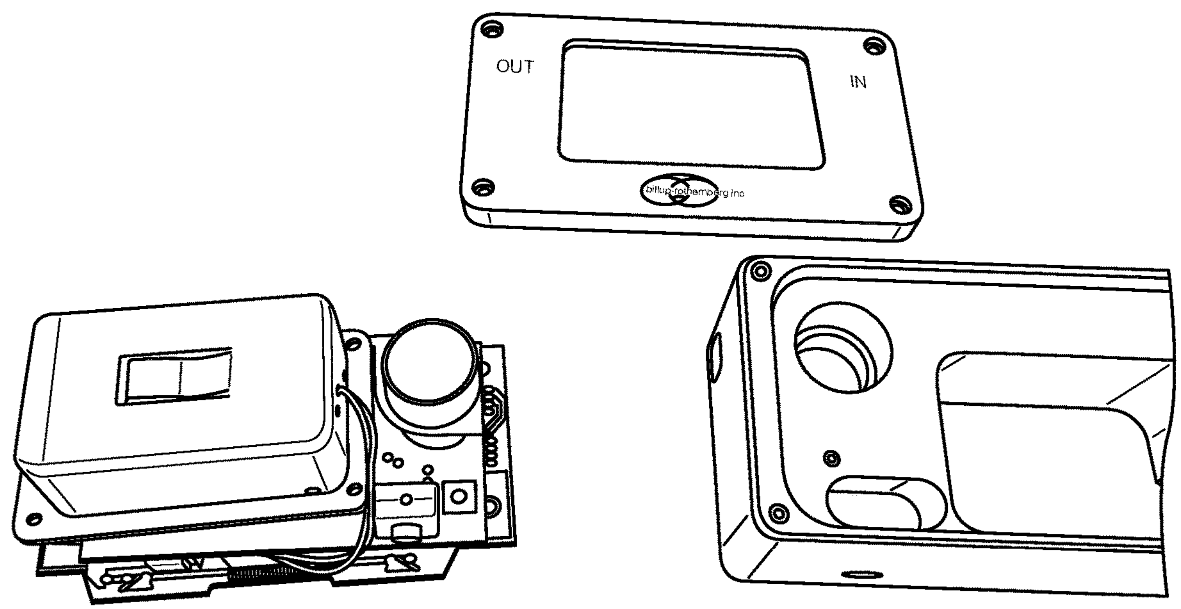
FIG. 6 discloses one exemplary embodiment of the different casing components of the gas mixing system along with an associated electronics module that includes memory and a microprocessor.

The low-pressure zone is the offset section on the left of the FIG. 3 provides more air volume so the pressure drops, this is enhanced by placing it right after the slight restriction imposed by the mixing baffles. As noted above, the reduced pressure compartment is fluidly coupled to the mixing chamber such that air passing by the reduced pressure compartment will experience a venturi-type effect (reduction in local pressure after leaving a constricted area) that will draw the gas stream into the reduced pressure compartment and further mix the gas stream for even more accurate measurements. FIG. 3 also depicts a comportment with associated electronic components that comprise a microprocessor and a memory to store the sensor data. FIG. 4 is an exemplary photograph of a static mixer having six repeating mixer elements. FIG. 5 exemplarily shows housing components and a display unit, while FIG. 6 exemplarily shows housing components and the electronics components of the device.

Embodiments of the present disclosure are further described in the following examples. The examples are merely illustrative and do not in any way limit the scope of the invention as claimed.

Example 1

Gas Mixing System

One embodiment of the gas mixing system is disclosed herein, illustrating the description and capabilities of the sensor, the benefits and features. In this embodiment, the system comprises an Oxygen Sensor, a barometric pressure sensor, a temperature sensor, and a humidity sensor.

The technology for the oxygen sensor comprises solid-state fluorescence quenching and diffusion sampling. The range of the oxygen sensor is 0% to 25% oxygen, the accuracy tolerance is less than 2% FS, and the resolution is 0.1%. The oxygen sensor can operate normally in temperatures ranging from −30° C. to 60° C., and pressure ranging from 500-1200 mbar.

The barometric pressure sensor disclosed in this example has a range between 500 to 1200 mbar, accuracy tolerance of 5 mbar, and resolution of 1 mbar.

The temperature sensor disclosed in this example has a range between −40° C. to 125° C., accuracy tolerance of ±0.2° C. (0° C. to 90° C.), resolution of 0.01° C., and maximum long-term drift of less than 0.03° C. per year.

The humidity sensor in this example has a range between 0% Relative Humidity (RH) to 100% RH, an accuracy tolerance of ±2% RH, resolution of 0.01% RH, hysteresis of ±0.8% RH (@25° C.), and typical long-term drift of less than 0.25% RH/year.

The gas mixing system disclosed herein is constructed from solid billet aluminum. It is factory calibrated, and maintenance free—no re-calibration required in normal operation. The system uses standard 9V battery for convenient replacement. Battery status and Low battery indicator are present on the display screen. For example, backlight would turn red when battery needs replacement.

There are several advantages of this gas mixing system disclosed herein, compared to currently known systems. For example, the instant system provides reliable and accurate performance; it has a long lifetime and therefore low maintenance; the solid state sensors have no moving parts, non-depleting technology; the system is easy to use, there are virtually no gas cross-sensitivity, works where other sensor technologies don't; it is vibration and shock resistant; compensated for temperature, humidity and pressure; and has a short warm-up time.

Example 2

Operation of the Gas Mixing System

This example provides one method of using the gas mixing system provided herein.

Step 1: Place 9V battery into black battery case on bottom of the gas mixing system enclosure.

Step 2: To turn the gas mixing system on, press the black power button, located on the front side of the enclosure.

Step 3: Allow the gas mixing system 2-3 minutes to stabilize. Display's bottom left corner counts down warmup time.

Step 4: Connect the gas lines from the two tanks to a Dual Flow Meter. The line from the 95% N2 & 5% CO2 tank connect to the bottom tubing connector of the 50 LPM flow meter. And the line from the 95% O2 & 5% CO2 is attached to the bottom tubing connector of the 2.5 LPM flow meter.

Step 5: After the bottom tubing is attached to the gas tanks, attach the upper tubing of the Dual Flow Meter with the red pressure release valve to the connector marked "IN" of the gas mixing system. The connector on the left side of enclosure marked "OUT" will be attached to the modular incubator chamber.

Step 6: Leave both white tubing clamps on the incubator in the OPEN position prior to mixing gases and flushing the modular incubator chamber. Failure to OPEN both white clamps will cause excessive pressure in the modular incubator chamber. The modular incubator chamber is not designed to be a pressure or vacuum chamber.

Step 7: To mix gases first predetermine the approximate flow rates of the 50 LPM and 2.5 LPM flow meters to obtain the percentage of oxygen needed for your experiments. Example: To obtain 5% 02, 5% CO2 and 90% N2 set the 50 LPM meter at 47.5 LPM and the 2.5 LPM meter set at 2.5 LPM.

Step 8: Open both tanks and adjust flow meters to the predetermined flow rate settings. Reading the GMS-5002, adjust the flow meters to obtain desired accurate percentage of oxygen.

Step 9: Flush 100 liters of gas through the modular incubator chamber containing desired percentage of oxygen.

Step 10: Shut off gas tanks and seal modular incubator chamber by closing white tubing clamps.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A gas mixing and analytic system, comprising:

a housing having a gas inlet and a gas outlet and a mixing chamber enclosed in the housing, wherein the mixing chamber is fluidly coupled between the gas inlet and the gas outlet;

wherein the gas inlet is coupled to a first gas source and a second gas source and configured to receive a premixed stream of gases from the first and second gas sources;

wherein the gas inlet delivers the premixed stream of gases to the mixing chamber that comprises a static mixer and a reduced pressure compartment downstream of the static mixer;

one or more sensors fluidly coupled to the reduced pressure compartment, wherein the one or more sensors are electronically coupled to a memory for data storage; and wherein the gas outlet is in fluid communication with the mixing chamber and is configured to discharge an intimately mixed gas stream formed from the premixed stream of gases.

2. The gas mixing and analytic system of claim 1, wherein the static mixer comprises a plurality of baffles.

3. The gas mixing and analytic system of claim 2 wherein the plurality of baffles are configured to split incoming gas at least four times.

4. The gas mixing and analytic system of claim 1, wherein the reduced pressure compartment comprises a portion having a lollipop shape.

5. The gas mixing and analytic system of claim 1, wherein the reduced pressure compartment comprises internal ridges.

6. The gas mixing and analytic system of claim 1, further comprising a display screen coupled to a microprocessor and operable to continuously display information sensed by the one or more sensors.

7. The gas mixing and analytic system of claim 1, wherein the first and second gas source provide two distinct gases selected from the group consisting of air, oxygen, nitrogen, argon, and carbon dioxide.

8. The gas mixing and analytic system of claim 7, wherein the first and second gas sources are further coupled to respective flow meters that control flow of the gases from the first and second gas sources, and wherein the respective flow meters are fluidly coupled to the gas inlet.

9. The gas mixing and analytic system of claim 7, wherein the gas inlet and the gas outlet are on opposite sides of the housing.

10. The gas mixing and analytic system of claim 1, wherein the mixing chamber has a volume of less than 50 ml.

11. A method of mixing two or more gases and determining the percentage of oxygen in the gas mixture, comprising:

providing from a first and a second gas source respective first and second gases, and feeding the first and second gases as a premixed stream of gases into a gas inlet of a mixing and analytic system;

wherein the mixing and analytic system comprises a housing with a gas inlet and a gas outlet and a mixing chamber that is fluidly coupled between the gas inlet and the gas outlet, wherein the mixing chamber comprises a static mixer that mixes the first and second gases to produce a gas mixture;

wherein the mixing chamber further comprises a reduced pressure compartment, and wherein one or more sensors are fluidly coupled to the reduced pressure compartment;

using the one or more sensors to determine the percentage of oxygen in the gas mixture while the mixed gas flows through the mixing and analytic system; and delivering the gas mixture as an intimately mixed gas stream formed from the premixed stream of gases though a gas outlet to an incubator, wherein the gas outlet is in fluid communication with the mixing chamber.

12. The method of claim 11, wherein flow of the first and second gases are individually regulated before entering the gas inlet.

13. The method of claim 11, wherein the static mixer comprises a plurality of baffles that mix the first and second gases to form a gas mixture.

14. The method of claim 13, wherein the gas mixture is fed past the reduced pressure compartment to generate a reduced pressure in the reduced pressure compartment.

15. The method of claim 11, further comprising further mixing the gas mixture in the reduced pressure compartment using internal ridges in the reduced pressure compartment.

16. The method of claim 11, further comprising continuously measuring at least oxygen content in the gas mixture using the one or more sensors and displaying the oxygen content on a display screen of the mixing and analytic system.

17. The method of claim 11, wherein feeding the first and second gases comprises adjusting flow of at least one of the first and second gases.

18. The method of claim 17, wherein the first and second gas sources are further coupled to respective flow meters that control flow of the gases from the first and second gas sources, and wherein the respective flow meters are coupled to the gas inlet.

19. The method of claim 17, wherein the premixed stream of gases comprises at least two gases selected from the group consisting of air, oxygen, nitrogen, argon, and carbon dioxide.

20. The method of claim 17, further comprising collecting and storing sensor data in a memory of the mixing and analytic system.

* * * * *